United States Patent [19]

Andrews et al.

[11] Patent Number: 5,219,887
[45] Date of Patent: Jun. 15, 1993

[54] DISINFECTING SHAMPOO COMPOSITION FOR ANIMALS

[75] Inventors: Jeffrey F. Andrews; Jane T. Kure, both of Stillwater, Minn.

[73] Assignee: Minnesota Mining and Manufacturing Company, St. Paul, Minn.

[21] Appl. No.: 893,666

[22] Filed: Jun. 4, 1992

Related U.S. Application Data

[63] Continuation-in-part of Ser. No. 712,915, Jun. 7, 1991, abandoned.

[51] Int. Cl.$^5$ .................. A61K 31/23; A61K 31/66
[52] U.S. Cl. ........................... 514/552; 514/549; 514/106; 514/881
[58] Field of Search ............... 514/552, 881, 106, 549, 514/517; 424/70; 252/106; 260/410.9 R, 413 R

[56] References Cited

U.S. PATENT DOCUMENTS

| | | | |
|---|---|---|---|
| 4,067,997 | 1/1978 | Kabara | 424/312 |
| 4,329,335 | 5/1982 | Su et al. | 252/DIG. 13 |
| 4,363,763 | 12/1982 | Peterson | 260/410.7 |
| 4,469,635 | 9/1984 | Peterson | 260/403 |
| 4,921,694 | 5/1990 | Hoppe et al. | 424/65 |

FOREIGN PATENT DOCUMENTS 243145 10/1987 European Pat. Off. .
0244144 1/1991 European Pat. Off. .

*Primary Examiner*—Marianne M. Cintins
*Assistant Examiner*—Rebecca Cook
*Attorney, Agent, or Firm*—Gary L. Griswold; Walter N. Kirn; Paul W. Busse

[57] ABSTRACT

A shampoo composition and related process for disinfecting, cleansing, conditioning, and moisturizing the skin and coat of an animal. The composition involves the use of a fatty acid monoester of a polyhydroxy alcohol, such as monolaurin, as an antimicrobial agent.

2 Claims, No Drawings

DISINFECTING SHAMPOO COMPOSITION FOR ANIMALS

This application is a continuation-in-part of U.S. patent application Ser. No. 07/712,915 filed Jun. 7, 1991, now abandoned.

TECHNICAL FIELD

The present invention relates to shampoos useful for cleansing and conditioning the hair and coat of animals. In another aspect, the invention relates to medicated shampoos, that is, shampoos that include the use of medicaments such as topical therapeutic agents, antimicrobial agents, and the like.

BACKGROUND OF THE INVENTION

Shampoos are commonly used for cleansing the coats of animals, e.g., domestic animals such as horses and cattle as well as cats and dogs. Typically it is necessary to use two or more separate products in order to cleanse, condition, and moisturize an animal's coat. The need to use several different products increases the expense of grooming the animal as well as the time spent grooming.

In addition to cleansing, shampoos may also be used to treat skin problems or diseases such as fungal or bacterial infections on domestic animals. For example, disinfecting shampoos generally include the use of medicaments, such as antimicrobial agents, in order to disinfect the coat of the animal while at the same time providing a cleansing effect. Currently available disinfecting shampoos for use on animals are commonly based on the use of either an iodophor or chlorhexadine as the active antimicrobial agent. Daily use of shampoos containing such active agents has been known to cause drying of the skin and hair, which both limits the frequency of use of the disinfecting shampoo and requires the use of conditioners or moisturizers.

What is clearly desirable and needed in the field is a single product that can be used to disinfect, cleanse, condition, and moisturize the coat of animals in a single application.

SUMMARY OF THE INVENTION

The present invention provides an antimicrobial shampoo composition for animals comprising a safe and effective stable emulsion of (a) an antimicrobial agent comprising a fatty acid monoester of a polyhydroxy alcohol, (b) a chelating agent, (c) a cleansing agent, (d) a conditioner, and (e) a moisturizer. Advantageously, this invention provides a medicated shampoo mild enough for everyday use as a prophylactic measure against fungal infection.

A preferred shampoo composition further comprises such adjuvants as a foam booster, a fragrance, a viscosity modifier, a coat shining agent, and/or a pearlizing agent. The single composition of the present invention provides an optimal combination of such properties as disinfecting, i.e., antimicrobial activity, cleansing, conditioning, and moisturizing, together with safety and efficacy, ease of storage and use, and esthetic properties.

It is presently preferred that the topical antimicrobial agent(s) used in the composition of the present invention include glyceryl fatty acid monoesters such as monolaurin (commercially available under the tradename LAURICIDIN). These monoesters are used in combination with a chelating agent, which agent may also serve as a moisturizer or moisturizing agent.

In another aspect, the present invention provides a process of safely and effectively disinfecting, cleansing, conditioning, and moisturizing the coat of an animal by the use of a single shampoo composition as described above. All of these features have not been previously available in one shampoo.

Shampoo compositions of the present invention are useful for a variety of animal applications, including humans, but are particularly useful for domestic animals such as horses, cattle, dogs, cats and the like. The shampoos of the present invention do not dry out hair or skin. This is in contrast to most commercially available antimicrobial shampoos, particularly those that rely on the use of iodine and chlorhexadine as the antimicrobial agent.

DETAILED DESCRIPTION OF THE INVENTION

The present invention provides an antimicrobial shampoo composition for animals comprising safe and effective compatible amounts of (a) an antimicrobial agent comprising a fatty acid monoester of a polyhydroxy alcohol, (b) a cleansing agent, (c) a conditioner, and (d) a moisturizer agent. A preferred shampoo composition further comprises such adjuvants as a foam booster, a fragrance, a viscosity modifier, a coat shining agent, and/or a pearlizing agent. A particularly preferred subclass of adjuvants are those characterized as "coat shiners".

As used herein the following words and terms, and inflections thereof, have the following meanings:

"shampoo" refers to a composition that is applied to the hair or coat of an animal, e.g., by scrubbing in the presence of added water, for use in disinfecting, cleansing, conditioning, and moisturizing the hair or coat;

"compatible" refers to a combination of components or ingredients that are therapeutically active and that form a stable emulsion that provides a desired combination of activity, safety, efficacy, and stability;

"disinfecting" refers to a shampoo that is able to kill, remove, inhibit, or otherwise reduce the number and/or growth rate of viable pathogenic microbes on or in the skin or coat of an animal;

"cleansing" refers to the ability of a shampoo to remove dirt and other extraneous or foreign matter from the skin or coat of an animal;

"conditioning" refers to the ability of a shampoo to provide a soft feel to the coat, and provide hairs that lay flat and are easily combable;

"moisturizing" refers to the ability of a shampoo to minimize to a desired extent whatever drying effect a shampoo might have on the skin or coat of an animal;

"shining" refers to the ability of a shampoo to provide a sheen or glossy appearance to the coat of an animal.

Shampoos of the present invention employ a safe and effective amount of an antimicrobial agent in combination with other ingredients of the shampoo in an aqueous solution. Such shampoo compositions typically employ about 0.01% to about 20% (by weight based on the total weight of the shampoo composition), preferably about 0.1% to about 10%, and most preferably about 1% to about 5% of a therapeutically active monoester.

Suitable antimicrobial agents for use in the composition of the present invention include fatty acid monoesters of polyhydroxy alcohols, such as fatty acid monoesters of glycerine, which are used in combination with a chelating agent or chelator. In other applications, such as food compositions and topical preparations, glyceryl fatty acid monoesters have been used, e.g., in combination with chelators, as antimicrobial agents. See, for example, U.S. Pat. Nos. 4,002,775, 4,067,997, and EPO Application No. 87303487.0 (corresponding to U.S. application Ser. No. 854,154, filed Apr. 21, 1986), and co-pending related U.S. application Ser. No. 509,316 (filed Apr. 13, 1990), the disclosures of each of which are hereby incorporated by reference. The presently preferred antimicrobial agent-chelator combinations are combinations of monolaurin and, as a chelator, a hydroxyalkanoic acid such as lactic acid or an acidic polyphosphate such as acidic sodium hexametaphosphate. Such combinations are preferred in view of their broad spectrum antimicrobial efficacy, relatively low cost, availability, and established safety.

The above fatty acid monoesters may also be used in combination with other fatty acids or mixtures of fatty acids in order to achieve increased gram negative activity. The preferred glyceryl fatty acid monoester may also be modified by the substitution of the glyceryl groups with certain ether substituent groups, particularly ethoxy and propoxy substituent groups. These substituted glyceryl fatty acid monoesters can also be used in combination with selected fatty acid mixtures as described in the above cited EPO and U.S. applications. Preferred glyceryl fatty acid monoesters for use in the present invention include monocaprin, monocaprylin, and monolaurin, and most preferred is monolaurin.

Also, fatty acid monoesters of other polyhydroxy alcohols such as propylene glycol, sucrose, glucose, sorbitol, and the like sugar esters work satisfactorily when substituted for the glyceryl fatty acid ester. The useful fatty acid esters or glyceryl fatty acid esters include those selected from the groups consisting of fatty acid esters or glyceryl fatty acid esters having about three to about thirty carbon atoms in the non-fatty acid moiety portion of the molecule; those that are monoesters and contain about three carbon atoms are preferred.

The glyceryl fatty acid monoester antimicrobial agents are preferred in that in addition to their activity and wide range, they have been found to be particularly compatible with the skin and coat of animals. In fact, it appears that they may often also serve as emollients. It has been observed, for instance, that the animal's coat is frequently softened, and the skin appears to be soothed, by the shampoos of the invention. Monolaurin appears to be quite effective for this purpose.

Esters such as those described above may undergo slow hydrolysis in aqueous solutions. In some cases certain of the hydrolysis products themselves may contribute antimicrobial activity. Reference to the concentration of such esters will be made to the compositions as originally prepared, i.e., without considering any hydrolysis that may occur on prolonged aging.

Preferred glyceryl fatty acid ester compounds include materials such as monocaprylin, monocaprin, monolaurin, and mixtures thereof. These materials may also be modified by the addition of one or more ethoxy/propoxy units prior to being employed in the combination. The tertiary mixtures useful herein comprise a glyceryl fatty acid ester (which can optionally be ethoxylated or propoxylated as described herein); a first fatty acid compound; and a second fatty acid compound.

The preferred first and second fatty acid compounds for use in such tertiary mixtures or combinations are preferably straight chain materials and include, without limitation, $C_6$ to $C_{14}$ saturated and $C_{13}$ to $C_{18}$ unsaturated fatty acids. The preferred saturated fatty acids include caproic, heptanoic, caprylic, pelargonic, capric, undecanoic, lauric and myristic. The most preferred materials include caproic, heptanoic, caprylic, capric, undecanoic, and lauric. Highly preferred materials include lauric, heptanoic, caprylic, and capric.

The preferred $C_{13}$ to $C_{18}$ unsaturated fatty acids are those having one or two cis type double bonds possessing the cis configuration, and mixtures of these materials. Particularly preferred materials include myristoleic, palmitoleic, linoleic, linolenic, and mixtures thereof.

The glyceryl fatty acid esters, first fatty acid, and second fatty acid are used in safe and effective amounts. In a preferred embodiment, they are present at a weight to weight ratio of ester to total fatty acid compounds of about 1:10 to about 10:1; more preferably about 1:10 to about 1:1, and still more preferably about 1:10 to about 1:5 with the glyceryl ester being present at a level of about 0.1% to about 5.0% of the final composition.

Cleansing agents useful in the composition and method of the present invention, e.g., as cleansing agents, include surfactants selected from the group consisting of sulfosuccinate esters such as dioctyl sodium sulfosuccinate; PLURONIC surfactants which are various commercially-available polyoxyethylene-polyoxypropylene copolymers (BASF Corp., Parsippany, N.J.); sodium lauryl sulfate and various alkoxylated derivatives known as sodium lauryl ether sulfates; cocamine derivatives such as dimethylcocamine oxide; polyoxyethylene cetyl ether; sorbitol esters such as sorbitan monolaurate; triethanolamine lauryl sulfate; sodium methyl cocoyl taurate; and mixtures thereof.

In a preferred embodiment the cleansing agents are dioctyl sodium sulfosuccinate, PLURONIC surfactants, e.g., PLURONIC "F68", sodium lauryl sulfate, sodium lauryl ether sulfate, and mixtures thereof, more preferred are PLURONIC "F68", sodium lauryl ether sulfate, sodium lauryl sulfate, and mixtures thereof.

The cleansing agents used in the shampoos of the present invention are used in relatively large amounts, e.g., about 20% to about 70% by weight, based on the weight of the total composition, and preferably about 40% to about 60% by weight. These agents are generally supplied commercially as aqueous solutions of the active ingredient, and the amounts of agent used is described as the amount of the commercially supplied solution. Alternatively, given the present teaching, a chemist skilled in the art can prepare and use any of the useful surfactants independently.

Preferred cleansing agents, e.g., sodium lauryl ether sulfate solutions, are generally supplied commercially as solutions of 15% to 60% sodium lauryl ether sulfate in water or water/ethanol. The term sodium lauryl ether sulfate as used by those skilled in the art refers to mixtures of alkoxylated sodium lauryl sulfate such as are generally commercially available.

Suitable conditioners for use in the shampoos of the invention are surfactants that are relatively hydrophilic, i.e., that contain organic substituents such as hydroxy substituents. An example of such a surfactant is sodium ososteroyl lactylate. Other suitable hair conditioners may be identified by those skilled in the art given the present teaching and include proteins, lanolin derivatives, silicone derivatives, and quaternary ammonium derivatives. A presently preferred hair conditioner is sodium isostearoyl lactylate, which is commercially available. The conditioner is generally used in an amount of about 1% to about 10%, and preferably about 4% to about 5% by weight based on the total weight of the shampoo composition.

Suitable moisturizing agents for use in the shampoo may be identified by those skilled in the art given the present teaching and include agents such as lanolin and its derivatives, emollient oils such as isopropyl myristate and isopropyl palmitate and the like, glycerin, propylene glycol, lactic acid, sodium lactate, partially ethoxylated glycerides (e.g., SOFTIGEN 767, a mixture of mono-, di- and triglycerides wherein the free hydroxy group is ethoxylated with ethylene oxide (Huls America, Inc., Piscatawny, N.J.), PATIONIC ISL sodium isostearoyl lactylate (R.I.T.A., Woodstock, Ill.), and glyceryl monolaurate. Preferred moisturizing agents include glyceryl monolaurate and lactic acid, since these materials serve dual purposes, i.e., as active antimicrobial agents and chelators respectively, in the shampoo.

Moisturizing agents may be used at a total concentration of between about 0% and about 20%, by weight based on the weight of the shampoo composition, and preferably between about 1% and about 10% by weight.

Suitable chelating agent(s) for use in the composition and process of the present invention include those selected from the group consisting of ethylenediamine tetraacetic acid ("EDTA"), $EDTA(Na)_2$, $EDTA(Na)_4$, hydroxyalkanoic acids such as lactic acid, acidic sodium hexametaphosphate (commercially available as SPORIX acidic sodium hexametaphosphate, from International Sourcing, Inc., Upper Saddle River, N.J.), and mixtures thereof. Lactic acid is preferred because it may function as both a chelator and a moisturizing agent in a composition of the present invention. The chelating agent is generally used in an amount of about 0.1% to about 5% and preferably about 0.5% to about 2% by weight based on the total weight of the shampoo composition.

Compositions of the present invention may optionally include a number of other adjuvants in order to provide improved and/or additional properties or features, to the extent such adjuvants do not detrimentally affect the composition to an extent that would make it unsuitable for its intended purpose. Examples of such adjuvants include foam boosters, fragrances, viscosity modifiers, coat shining agents, pearlizing agents, thickening agents, dyes, and the like.

The foam booster(s) of the compositions of the present invention are generally nonionic surfactants with a hydrophilic nature such as amides, e.g., cocodiethanolamide and long chain PLURONIC surfactants, and highly foaming anionic surfactants such as sodium lauryl sulfate. As will become apparent to those skilled in the art, certain of the surfactants useful as surface cleansing agents and described above will have some foam boosting activity as well.

The term "foam booster", as used herein, refers to an ingredient that serves to increase the amount and/or stability of the foam or lather of a composition of the present invention. A presently preferred foam booster of the invention is cocodiethanolamide. Foam boosters are used in the amounts suitable to achieve the desired effect, and are generally used in an amount of about 1% to about 10% and preferably about 2% to about 4% by weight, based on the total weight of the shampoo composition.

The word "fragrance", as used herein, refers to an ingredient that serves to mask any undesirable odors of other components of a composition of the present invention, and/or simply to provide an appealing odor. Suitable fragrances will become apparent to those skilled in the art. Some fragrances which have been selected as particularly suitable for use in the present invention include MUSK 3210E (Santell Corp.) and HERBAL FRAGRANCE (Universal Flavors, Inc.). Fragrances are generally relatively potent chemicals and require only small amounts, e.g., about 0.01% to about 2% by weight based on the total weight of the shampoo composition, and preferably about 0.05% to about 1%, to achieve the intended effect.

Suitable viscosity modifiers are generally organic solvents that are at least partially soluble in water, and that are used to reduce gelling and excessive thickening of the shampoo. The term "viscosity modifier" as used herein refers to an ingredient that serves to alter the viscosity of a composition so as to achieve a desired viscosity. Relatively small amounts of viscosity modifiers are generally used, but it will become apparent to those skilled that the selection and amount of viscosity modifier depends upon the types and amounts of the other ingredients and the viscosity desired for the shampoo. User preference has a strong influence on the viscosity selection. For some animals a thicker, more viscous shampoo might be desired, e.g., for horses and other animals having short hair, while for longer haired animals a less viscous shampoo may be preferred.

In preferred shampoos of the present invention the amount of viscosity modifier is generally about 0.1% to about 5%, and preferably about 0.5% to about 2% by weight, based on the total weight of the shampoo composition. A preferred viscosity modifier is propylene glycol. The viscosity is generally in the range of about 1000 cps to about 4000 cps, preferably about 1200 cps to about 3800 cps, and most preferably about 1400 cps to about 2600 cps.

Optional adjuvants may also be used to achieve variations in appearance, such as dyes, and appearance modifiers, e.g., ethylene glycol distearate and ethylene glycol monostearate which give a "pearly" or glistening appearance to some shampoo formulations.

Other adjuvants that may be used in shampoos include antioxidants, thickening agents, solubilizers, abrasion agents and the like. Thickening agents include sodium chloride, gums such as xanthan gum and polymers such as those of the CARBOPOL series.

Compositions of the present invention can be prepared using techniques within the skill of those in the art. The various ingredients may be combined in any suitable manner, including in the manner described further in the EXAMPLES below. The compositions contain added water as a diluent generally about 25% to about 75% (and preferably about 35% to about 50%) by weight based on the total weight of the entire shampoo composition. The water is generally deionized or distilled, or is otherwise relatively pure water, in order to avoid adding unknown ingredients to the composition that might affect the properties of the medicated shampoos of the present invention.

The process of the present invention, also described more fully in the EXAMPLES below, involves the use of a composition as described herein to shampoo an animal. The composition is used in contact with the coat of the animals and preferably in combination with added water, to scrub the composition into the coat for a sufficient time and in a sufficient manner, e.g., by working up a lather, to create a disinfecting, cleansing, and conditioning effect.

The antimicrobial action of the shampoos of the invention has been demonstrated by testing samples of the shampoos against various bacteria and fungi known to be present on animal hair and skin. Standardized tests have demonstrated acceptable in vitro antimicrobial activity of the shampoos, even when diluted as much as 128:1 with water.

The shampoos of the present invention have been found to be active against a variety of microbes such as gram negative and gram positive bacteria, yeast, and fungi, including the following common fungal species: *Trichophyton equinum, Trichophyton mentagrophytes, Trichophyton verrucosum, Microsporum canis, Microsporum gypseum,* and *Malasezzia canis.*

The shampoos of the present invention have also been found to be active against a variety of bacteria including: *Staphylococcus aureus, S. intermedius,* and *S. epidermidis, Streptococcus agalactiae, S. uberis.* and *S. pyogenes, Escherichia coli, Salmonella typhimurium, Klebsiella pneumoniae,* and *Pseudomonas aeruginosa.*

These fungi and bacteria serve as indicator species to demonstrate a wide spectrum of antimicrobial activity for the shampoos of the present invention.

The following EXAMPLES are provided solely to illustrate the invention. They are not intended to limit the invention defined by the appended claims. All percents used are percents by weight of the identified ingredient based on the weight of the composition, unless otherwise stated.

EXAMPLE 1

Preparation of Shampoo Compositions

Three different compositions of the present invention were made using the following general procedure. To a stirred beaker containing a known weight of water at about 71° C. was added a weighed amount of sodium lauryl ether sulfate as a cleansing agent, after which at five minute intervals weighed amounts of each of the remaining ingredients in TABLE 1 were added. The mixture was cooled to about 43° C. and then the fragrance was added. In Composition B the green dye was added last.

TABLE 1

| Ingredient | Comp. A (%) | Comp. B (%) | Comp. C (%) |
| --- | --- | --- | --- |
| Antimicrobial agent: LAURICIDIN (Monolaurin) (Lauricidin Inc., Monroe, MI) | 2.0 | 2.0 | 2.0 |
| Chelator: Lactic acid | 1.5 | 1.5 | 1.0 |
| Surface cleansing agents: | | | |
| TAURANOL WS Surfactant Concentrate (Finetex, Inc., Elmwood Part, NJ) | 0 | 0 | 15.0 |
| Sodium lauryl ether sulfate (SIPON ES-2, Rhone-Poulenc, Canbury, NJ) | 53.0 | 53.0 | 15.0 |
| Hair conditioners: | | | |
| FINEQUAT CT surfactant composition (Finetex, Inc.) | 0 | 0 | 5.0 |
| PATIONIC ISL (Sodium isostearoyl lactylate) (R.I.T.A., Woodstock, IL) | 4.0 | 4.0 | 0 |
| Foam booster: MACKAMIDE C (Cocodiethanolamide) | 0 | 2.0 | 5.0 |

TABLE 1-continued

| Ingredient | Comp. A (%) | Comp. B (%) | Comp. C (%) |
| --- | --- | --- | --- |
| (McIntyre Chemical Co., Chicago, IL) | | | |
| Fragrance: Herbal fragrance (Universal Flavors, Inc., Indianapolis, IN) | 0 | 25 drops | 0 |
| Viscosity modifier: Propylene glycol | 1.0 | 1.0 | 0 |
| Dye: FDC Green No. 3 (H. Kohnstamn, New York, NY) | 0 | 0.1 g | 0 |
| Deionized water | 38.5 | 36.5 | 57.0 |

Composition A was a white lotion. Composition B was initially a white lotion, but changed to a green lotion upon addition of dye. Composition C was a white lotion, having a viscosity noticeably lower than Compositions A and B.

EXAMPLE 2

Use of Shampoo Compositions

Composition A of EXAMPLE 1 was evaluated for efficacy by rinsing both sides of a horse with warm water, then lathering one side with the shampoo of Composition A and the other side with a commercially available shampoo, FARNAM'S WONDER BLUE (Farnam Co., Phoenix, Ariz.). Each shampoo was rinsed from the horse's hair with warm water, then the hair was allowed to air dry (air temperature was about 27° C., relative humidity about 60%) for about 60 minutes.

The tail of the horse was also washed using Composition A, then combed. It combed very readily without the aid of a further conditioner treatment.

During the lathering, Composition A provided less overall foam, and the duration of foaming was shorter than the commercial shampoo. The hair cleaned by Composition A was shinier, and the coat, mane and tail felt softer, silkier, and smoother. The hair cleaned by Composition A also dried more slowly, indicating an ability to both hold water longer and moisturize longer.

The coat of the horse that had been washed by the two different shampoos was evaluated by a total of five individual observers. Each agreed that the shampoo of the present invention provided an improved result based on both feel and appearance.

EXAMPLE 3

Shampoo Composition Having Alternative Surface Cleansing Agents

Three variations of a shampoo composition of the invention were made using the general procedure described in EXAMPLE 1, and the ingredients shown in TABLE 2.

TABLE 2

| Ingredient | Comp. D (%) | Comp. E (%) | Comp. F (%) |
| --- | --- | --- | --- |
| Antimicrobial agents: | | | |
| LAURICIDIN | 2.0 | 1.0 | 1.0 |
| BHA (Butylated hydroxyanisole, Eastman Chemical Products, Kingsport, TN) | 0.2 | 0 | 0 |
| EMERY 658 (caprylic/capric acids, Emery Chemicals, Los Angeles, CA) | 0 | 0 | 1.0 |
| Chelator: Ethylenediamine tetraacetic acid tetrasodium salt | 0.2 | 0.1 | 0.1 |

TABLE 2-continued

| Ingredient | Comp. D (%) | Comp. E (%) | Comp. F (%) |
|---|---|---|---|
| Cleansing agents: | | | |
| MACKADET SBC-8 (shampoo base, McIntyre Chemical Co.) | 40.0 | 0 | 0 |
| MACKANATE EL (disodium laureth sulfosuccinate, McIntyre Chemical Co.) | 0 | 0 | 30.0 |
| Cleansing agent and foam booster: CYCLORYL NWC (shampoo base of sodium lauryl ether sulfate, "Cocamide DEA" and triethanolamine lauryl sulfate, Alcolac, Baltimore, MD) | 0 | 60.0 | 0 |
| Conditioners: | | | |
| MACKAM WGB (Wheat germ betaine, McIntyre Chemical Co.) | 5.0 | 0 | 5.0 |
| LANETO 100 (PEG-75 Lanolin, R.I.T.A. Corp., Woodstock, IL) | 2.0 | 2.0 | 0 |
| Foam booster: MACKAMIDE C | 0 | 0 | 2.0 |
| Deionized Water | 50.6 | 36.9 | 60.9 |

The shampoo of Composition D was a clear yellow-amber solution having a satisfactory viscosity. The shampoo of Composition E was a clear yellow solution having an almost gel-like viscosity. The shampoo of Composition F was a clear yellow having a soapy smell and relatively low viscosity.

EXAMPLE 4

Shampoo Composition Having Alternative Chelating Agents

A variation of a shampoo composition of the invention was made using the general procedure described in EXAMPLE 1 and the ingredients shown in TABLE 3.

TABLE 3

| Ingredient | Comp. G (%) |
|---|---|
| Antimicrobial agents: LAURICIDIN | 2.0 |
| Chelator: | 2.0 |
| SPORIX Acidic sodium hexametaphosphast (International Sourcing, Inc., Upper Saddle River, NJ) | |
| Cleansing agents: | |
| SIPON ES-2 (Rhone-Poulenc Corp., Canbury, NJ) | 30 |
| PLURONIC F-68 (BASF Corp., Parsippany, NJ) | 10 |
| Conditioner: | 4.0 |
| PATIONIC ISL (R.I.T.A , Woodstock, IL) | |
| Moisturizer: Sodium lactate | 2.0 |
| Foam booster: MACKAMIDE C (McIntyre Chemical Co., Chicago, IL) | 2.0 |
| Pearlizing agent: Ethylene glycol distearate | 2.0 |
| Distilled water | 46.0 |

When used on dogs and cats, Composition G provides a coat that is silky and shining. Furthermore, no difference in the coats of cats and dogs was observed when Composition G was used on the animals compared to use of ALLEGROOMS non-medicated grooming shampoo (Virbac Inc., Forth Worth, Tex.) on the animals.

EXAMPLE 5

Use of Compositions

The shampoos of Compositions C and D were evaluated and compared, as described in EXAMPLE 2, on opposite sides of a horse. Composition C was also used to wash the tail of the horse. Composition C provided more foam than the shampoo of Composition D. The horse was rinsed with warm water and allowed to air dry, which took approximately 45 minutes (air temperature was about 30° C. and the relative humidity was about 60%).

Evaluation of the feel and appearance of the hair of the horse by 5 observers resulted in the consensus that the shampoo of Composition D provided a silkier feel, but two observers still preferred the overall results of the shampoo of Composition A as described in EXAMPLE 2. The tail combed out readily, but did not feel as silky as when the shampoo of Composition A was used as described in EXAMPLE 2.

EXAMPLE 6

Use of Compositions Having Foam Booster and Fragrance

The shampoo of Composition A as described in EXAMPLE 1, and the shampoo of Composition H described in Example 7, below, were evaluated in the manner described in EXAMPLE 2 on opposite sides of a horse. These two compositions differ only in that a foam booster and fragrance were added to provide Composition H. The shampoo of Composition H provided more foam and was removed more readily when rinsing after washing. The shampoo of Composition H was used to wash the tail of the horse, then the tail was rinsed.

A fan was used to accelerate drying, by having the horse face the fan. Humidity was high (about 68%) and temperature was about 28° C. and drying required about one hour.

Evaluation of the feel and appearance of the horse's hair by five observers resulted in the consensus that the shampoo of Composition H provided hair that was as silky and shiny as for Composition A described earlier, but the increased amount of foam booster helped the perceived cleaning ability of Composition H. The tail combed out readily and was silky to the touch. The musk fragrance was observed as well and was described as clean and fresh.

EXAMPLE 7

Effect of Varying the Source of Surface Cleansing Agent

Two compositions of the invention were made using the same general procedure described above and the ingredients shown in TABLE 4, only varying the source of the sodium lauryl ether sulfate. The procedure used was as follows: The water was heated to 160±5° F. (about 70° C.) then stirred while slowly adding the respective sodium lauryl ether sulfate. The lactic acid and propylene glycol were added while heating the solution back to 160° F. The sodium isostearoyl lactylate (PATIONIC ISL) was warmed to 115° to 120° F. (about 46° C.) and added to the 160° F. solution. The cocodiethanolamide (MACKAMIDE C) was added 5 minutes after the completion of the addition of PATIONIC ISL conditioner. Melted ethylene glycol distearate ("EGDS") was added to the solution 5 minutes after the completion of the addition of the MACKAMIDE C foam booster. The LAURICIDIN antimicrobial agent was then added slowly to the solution. The solution was allowed to cool to about 100° to 110° F. (about 40° C.) and the musk fragrance was added. Mixing was continued for 30 minutes.

TABLE 4

| Ingredient | Comp. H (%) | Comp. I (%) |
| --- | --- | --- |
| Antimicrobial agent: LAURICIDIN | 2.0 | 2.0 |
| Chelator: Lactic Acid | 1.5 | 1.5 |
| Surface cleansing agents: | | |
| Sodium lauryl ether sulfate (STANDOPOL ES-2, Henkel Corp., Ambler, PA) | 53.0 | 0 |
| Sodium lauryl ether sulfate (SIPON ES-2, Rhone-Poulenc Corp., Canbury, NJ) | 0 | 53.0 |
| Conditioner: PATIONIC ISL | 4.0 | 4.0 |
| Foam booster: MACKAMIDE C | 2.0 | 2.0 |
| Fragrance: MUSK FRAGRANCE 3210E (Santell Corp., Chicago, IL) | 0.3 | 0.3 |
| Viscosity modifier: Propylene Glycol | 1.0 | 1.0 |
| Pearlizing agent: Ethylene glycol distearate ("EGDS") | 1.0 | 1.0 |
| Deionized Water | 35.2 | 35.2 |

The pH of each composition was determined using a CORNING METER 125 pH meter with 2 calibrations at pH 4 and pH 7. Readings were taken after 1 minute equlibration and found to be pH 3.86 for Composition G and pH 3.68 for Composition H. Viscosity was measured for each composition and determined by using a BROOKFIELD LVT viscometer, without the guard, using spindle #4 at 60 rpms. An average of 3 recordings was determined to be 2360 cps for Composition H and 2507 cps for Composition I.

Compositions H and I were both viscous, white liquids having a pearly sheen.

EXAMPLE 8

Antimicrobial Activity

A batch of the shampoo composition of the invention (identical to Composition I although having 0.2% musk fragrance and 35.3% deionized water) was evaluated for antimicrobial effectiveness against both bacteria and fungi. As can be seen in TABLE 5 below, the shampoo was found to be useful for killing both bacteria and fungi. The evaluation used was performed according to the general method of the National Mastitis Council test, as described in the November 1977 Proposed Guideline to Determine Biocidal Activity within a Teat Dip Solution as a Modification of the Germicidal and Detergent Sanitizer Test Official Methods of Analysis, A.O.A.C. Twelfth Edition, Section 4.023-4.032; pp. 63-65, 1975, the disclosure of which is incorporated herein by reference.

The bacteria were essentially completely killed with 5 minutes by the shampoo. Because large initial inoculum counts of most of the fungi could not be obtained, and because of the tendency of the fungi to swarm over the plates, the log reductions reported for all fungi except *M. canis* are provided as approximate values.

TABLE 5

Kill Rates for Shampoo Against Bacteria and Fungi

| Organism | Log Reduction at 25° C. | | |
| --- | --- | --- | --- |
| | 2 min. | 5. min. | 10 min. |
| S. aureus | 3.36 | >4.44 | 4.31 |
| P. aeruginosa | >4.39 | >4.39 | >4.39 |
| E. coli | >5.72 | >5.72 | >5.72 |
| M. gypseum | 1.10 | 1.15 | 1.14 |
| Microsporum canis | 1.75 | 2.08 | 2.32 |
| Malasezzia canis | 2.18 | 2.48 | >3.10 |
| T. mentagrophytes | 0.10 | 0.91 | 1.51 |
| T. equinum | 0.23 | 0.66 | 1.67 |

What is claimed is:

1. An antimicrobial shampoo composition comprising a stable emulsion of
   i) 0.01-20 wt. % of an antimicrobial agent comprising a fatty acid monoester of a polyhydroxy alcohol,
   ii) 0.1-5 wt. % of a chelating agent selected from the group consisting of ethylenediamine tetraacetic acid and salts thereof, lactic acid, and acidic polyphosphates,
   iii) 20-70 wt. % of a cleansing agent selected from the group consisting of sulfosucciante esters, polyoxyethylene-polyoxypropylene copolymer surfactants, sodium lauryl sulfate and derivatives thereof, polyoxyethylene cetyl ether, sorbital esters, triethanolamine lauryl sulfate, sodium cocoyl taurate, and mixtures thereof,
   iv) 1-10 wt. % of sodium isostearoyl lactylate,
   v) 1-10 wt. % of a moisturizer selected from the group consisting of lactic acid and sodium lactate, and
   vi) 25-75 wt. % water.

2. A method for cleansing, conditioning, disinfecting, and moisturizing the coat of an animal comprising the steps of
   a) contacting the coat of the animal in the presence of water with a single composition comprising a stable emulsion of claim 1.

* * * * *

UNITED STATES PATENT AND TRADEMARK OFFICE
CERTIFICATE OF CORRECTION

PATENT NO. : 5,219,887
DATED : June 15, 1993
INVENTOR(S) : Jeffrey F. Andrews; Jane T. Kure It is certified that error appears in the above-indentified patent and that said Letters Patent is hereby corrected as shown below:

Col. 4, line 65  "osostearoyl" should read --isostearoyl--

Signed and Sealed this

Twenty-second Day of February, 1994

Attest:

BRUCE LEHMAN

Attesting Officer   Commissioner of Patents and Trademarks